United States Patent
Pedroso et al.

(10) Patent No.: US 12,226,591 B2
(45) Date of Patent: *Feb. 18, 2025

(54) CATHETER WITH TEXTURED SURFACE

(71) Applicant: DePuy Synthes Products, Inc., Raynham, MA (US)

(72) Inventors: Pedro Pedroso, Parkland, FL (US); Chadwin Hanna, Jr., Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/374,824

(22) Filed: Sep. 29, 2023

(65) Prior Publication Data

US 2024/0024625 A1    Jan. 25, 2024

Related U.S. Application Data

(63) Continuation of application No. 17/114,788, filed on Dec. 8, 2020, now Pat. No. 11,786,698.

(51) Int. Cl.
*A61M 25/00* (2006.01)

(52) U.S. Cl.
CPC ... *A61M 25/0052* (2013.01); *A61M 2025/006* (2013.01); *A61M 2210/12* (2013.01)

(58) Field of Classification Search
CPC .......... A61M 25/0009; A61M 25/0012; A61M 25/0015; A61M 25/0043; A61M 25/0051;
(Continued)

(56) References Cited

U.S. PATENT DOCUMENTS

| 4,981,478 A | 1/1991 | Evard et al. |
| 5,102,402 A | 4/1992 | Dror |

(Continued)

FOREIGN PATENT DOCUMENTS

| EP | 1 707 234 A1 | 10/2006 |
| EP | 3 583 972 A2 | 12/2019 |

(Continued)

*Primary Examiner* — Emily L Schmidt
*Assistant Examiner* — Antarius S Daniel
(74) *Attorney, Agent, or Firm* — Troutman Pepper Locke LLP (57) ABSTRACT

A catheter can have a textured outer body surface with protrusions and/or indentations that can reduce friction between the outer body surface and vascular anatomy or an inner lumen of another catheter in contact with the outer body surface. The catheter can include protrusions and/or indentations on an inner lumen surface that can reduce friction between the inner lumen surface and an outer body surface of another catheter within the example catheter. The protrusions can be filled with a lubricant or vasodilating drug, and the protrusions can be configured to break to release the fluid in response to forces on the protrusion during navigation through vascular anatomy and/or an inner lumen of another catheter. The catheter can include a metallic tubular reinforcing layer with openings through which the protrusions and/or indentations extend and/or protrusions and/or indentations shaped into the reinforcing layer.

19 Claims, 6 Drawing Sheets

(58) Field of Classification Search
CPC ............ A61M 25/005; A61M 25/0053; A61M 25/00; A61M 2025/0057; A61M 2025/006; A61M 2025/0062
See application file for complete search history.

(56) References Cited

U.S. PATENT DOCUMENTS

| | | | |
|---|---|---|---|
| 5,125,909 A | 6/1992 | Heimberger | |
| 5,244,619 A * | 9/1993 | Burnham | A61M 25/005 264/171.2 |
| 5,403,292 A | 4/1995 | Ju | |
| 5,454,795 A | 10/1995 | Samson | |
| 5,658,264 A | 8/1997 | Samson | |
| 5,885,508 A | 3/1999 | Ishida | |
| 5,897,537 A | 4/1999 | Berg et al. | |
| 5,938,587 A | 8/1999 | Taylor et al. | |
| 5,947,940 A | 9/1999 | Beisel | |
| 6,027,863 A | 2/2000 | Donadio, III | |
| 6,221,059 B1 | 4/2001 | Chiang et al. | |
| 6,352,531 B1 | 3/2002 | O'Connor et al. | |
| 6,391,037 B1 | 5/2002 | Greenhalgh | |
| 6,551,239 B2 | 4/2003 | Renner et al. | |
| 6,749,560 B1 | 6/2004 | Konstorum et al. | |
| 7,722,545 B2 | 5/2010 | Bertsch | |
| 7,771,410 B2 | 8/2010 | Venturelli | |
| 7,833,203 B2 | 11/2010 | Sherman et al. | |
| 7,914,466 B2 | 3/2011 | Davis et al. | |
| 8,585,643 B2 | 11/2013 | Vo et al. | |
| 9,144,665 B2 | 9/2015 | Salstrom et al. | |
| 9,232,992 B2 | 1/2016 | Heidner | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li et al. | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 9,974,926 B2 | 5/2018 | Northrop et al. | |
| 10,219,887 B2 | 3/2019 | Johnson et al. | |
| 10,617,847 B2 | 4/2020 | Cottone et al. | |
| 2002/0087076 A1 | 7/2002 | Meguro et al. | |
| 2004/0122415 A1* | 6/2004 | Johnson | A61M 25/0023 604/528 |
| 2004/0153049 A1 | 8/2004 | Hewitt et al. | |
| 2006/0030835 A1* | 2/2006 | Sherman | A61M 25/0053 604/526 |
| 2006/0064151 A1 | 3/2006 | Guterman | |
| 2006/0264905 A1 | 11/2006 | Eskridge et al. | |
| 2007/0255255 A1 | 11/2007 | Shah et al. | |
| 2008/0097398 A1 | 4/2008 | Mitelberg et al. | |
| 2008/0188928 A1 | 8/2008 | Salahieh et al. | |
| 2008/0281350 A1 | 11/2008 | Sepetka | |
| 2010/0063479 A1 | 3/2010 | Merdan et al. | |
| 2010/0324649 A1 | 12/2010 | Mattsson | |
| 2011/0152765 A1 | 6/2011 | Weber et al. | |
| 2012/0101480 A1 | 4/2012 | Ingle et al. | |
| 2012/0283768 A1 | 11/2012 | Cox et al. | |
| 2013/0046285 A1 | 2/2013 | Griffin et al. | |
| 2014/0052108 A1 | 2/2014 | De Kock et al. | |
| 2014/0135812 A1 | 5/2014 | Divino et al. | |
| 2014/0200607 A1 | 7/2014 | Sepetka et al. | |
| 2015/0080858 A1 | 3/2015 | Moss | |
| 2015/0231367 A1 | 8/2015 | Salstrom et al. | |
| 2015/0258305 A1* | 9/2015 | Dye | A61M 25/0017 604/544 |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu et al. | |
| 2017/0027640 A1 | 2/2017 | Kunis et al. | |
| 2017/0027692 A1 | 2/2017 | Bonhoeffer et al. | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0071737 A1 | 3/2017 | Kelley | |
| 2017/0072452 A1 | 3/2017 | Monetti et al. | |
| 2017/0079671 A1 | 3/2017 | Morero et al. | |
| 2017/0079680 A1 | 3/2017 | Bowman | |
| 2017/0079766 A1 | 3/2017 | Wang et al. | |
| 2017/0079767 A1 | 3/2017 | Leon-Yip | |
| 2017/0079812 A1 | 3/2017 | Lam et al. | |
| 2017/0079817 A1 | 3/2017 | Sepetka et al. | |
| 2017/0079819 A1 | 3/2017 | Pung et al. | |
| 2017/0079820 A1 | 3/2017 | Lam et al. | |
| 2017/0086851 A1 | 3/2017 | Wallace et al. | |
| 2017/0086996 A1 | 3/2017 | Peterson et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Granfield | |
| 2017/0100183 A1 | 4/2017 | Iaizzo et al. | |
| 2017/0113023 A1 | 4/2017 | Steingisser et al. | |
| 2017/0147765 A1 | 5/2017 | Mehta | |
| 2017/0151032 A1 | 6/2017 | Loisel | |
| 2017/0165062 A1 | 6/2017 | Rothstein | |
| 2017/0165065 A1 | 6/2017 | Rothstein et al. | |
| 2017/0165454 A1 | 6/2017 | Tuohy et al. | |
| 2017/0172581 A1 | 6/2017 | Bose et al. | |
| 2017/0172766 A1 | 6/2017 | Vong et al. | |
| 2017/0172772 A1 | 6/2017 | Khenansho | |
| 2017/0189033 A1 | 7/2017 | Sepetka et al. | |
| 2017/0189035 A1 | 7/2017 | Porter | |
| 2017/0215902 A1 | 8/2017 | Leynov et al. | |
| 2017/0216484 A1 | 8/2017 | Cruise et al. | |
| 2017/0224350 A1 | 8/2017 | Shimizu et al. | |
| 2017/0224355 A1 | 8/2017 | Bowman et al. | |

(56) References Cited

U.S. PATENT DOCUMENTS

| | | |
|---|---|---|
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296221 A1* | 10/2017 | Di Caprio .............. A61M 25/01 |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0126119 A1* | 5/2018 | McNiven .......... A61M 25/0136 |
| 2020/0222664 A1 | 7/2020 | Cottone et al. |

FOREIGN PATENT DOCUMENTS

| | | |
|---|---|---|
| JP | 2001-161631 A | 6/2001 |
| JP | 2012-20068 A | 2/2012 |
| JP | 2014-236863 A | 12/2014 |
| KR | 10-2010-0098404 A | 9/2010 |
| WO | WO 96/33763 A2 | 10/1996 |
| WO | WO 2017/027161 A1 | 2/2017 |
| WO | WO 2020/055448 A1 | 3/2020 |
| WO | WO 2020/175462 A1 | 9/2020 |

* cited by examiner

CATHETER WITH TEXTURED SURFACE

CROSS REFERENCE TO RELATED APPLICATION

The present application is a continuation application of U.S. patent application Ser. No. 17/114,788 filed Dec. 8, 2020. The entire contents of which are hereby incorporated by reference.

FIELD

The present invention relates to medical devices and treatments and more specifically to catheters.

BACKGROUND

Catheters serve a broad range of functions in intravascular medical treatments. Catheters are typically a tube manufactured from medical grade materials that can be inserted into a body and can be used to deliver drugs or other devices, perform surgical procedures, remove blockages from vessels, and a variety of other purposes. By modifying the material or adjusting the way a catheter is manufactured, it is possible to tailor different sections of the catheter for particular applications.

When navigation through vascular anatomy or through an inner lumen of another catheter contact between an exterior surface of the catheter and vasculature or the inner lumen of another catheter creates friction. The resulting friction determines an amount of tracking force required to move the catheter. Too much friction or tracking force can cause the catheter to become lodged, damage tissue, or kink the catheter. Further, vasospasms can occur when navigating a catheter through neuro vasculature which can cause procedural delays.

SUMMARY

Examples presented herein generally include a catheter having a textured outer body surface with protrusions and/or indentations that can reduce friction between the outer body surface and vascular anatomy or an inner lumen of another catheter in contact with the outer body surface. The catheter can additionally, or alternatively, include protrusions and/or indentations on an inner lumen surface that can reduce friction between the inner lumen surface and an outer body surface of another catheter or a device within the example catheter. The protrusions and/or indentations can be sized, shaped, positioned, and otherwise configured to affect a flexibility gradient of the catheter. The protrusions can be filled with a lubricant or vasodilating drug and the protrusions can be configured to break to release the fluid when force is applied. For instance, protrusions can burst in response to forces on the protrusion during navigation through vascular anatomy and/or an inner lumen of another catheter. Some example catheters can include a metallic tubular reinforcing layer. The metallic tubular reinforcing layer can include openings through which the protrusions and/or indentations extend. Additionally, or alternatively, protrusions and/or indentations can be shaped into the reinforcing layer.

An example catheter can include a first tubular surface, a second tubular surface opposite the first tubular surface, and deformations each including an indentation on the first surface and a corresponding protrusion on the second surface opposite the indentation.

The indentation and corresponding protrusion of each of the deformations can be respectively hemispherical in shape.

The first surface can be an interior surface of the catheter and the second surface can be an exterior surface of the catheter. Alternatively, the first surface is the exterior surface of the catheter and the second surface is the interior surface of the catheter. As another alternative, the catheter can be configured such that the exterior surface includes both indentations and protrusions and the interior surface includes both protrusions and indentations corresponding to the indentations and protrusions on the exterior surface to form respective deformations.

A first region of the catheter can include some or all of the deformations spaced in a regular pattern. A second region of the catheter can lack deformations, can be substantially smooth at least on the exterior surface of the catheter, and can have an area sufficiently large to interrupt the regular pattern of the deformations in the first region. When the exterior of the catheter including the first and second regions is applied to vascular tissue, contact between the second region and vascular tissue can result in a higher coefficient of static friction compared to coefficient of static friction between the first region and vascular tissue.

The catheter can further include an inner liner, a braided wire support structure disposed around the inner liner, and an outer polymer layer disposed around the braided wire support structure. The catheter can further include a metallic tubular reinforcing layer disposed around the braided wire support structure. The outer polymer layer can be disposed around the metallic tubular reinforcing layer.

The deformations can be shaped by the inner liner, braided wire support structure, and the outer polymer layer. The metallic tubular reinforcing layer can have sidewall openings through which the inner layer, braided wire support structure, and outer polymer layer protrude to shape at least one of the deformations. Some of the sidewall openings can have a circular shape with a circumference. Some of the deformations protruding through the sidewall opening can have a hemispherical shape having a circumference about equal to that of the circumference of the circular shape of the sidewall opening. Some of the sidewall openings can have a helical shape circumscribing the catheter.

Some deformations can be shaped by the metallic tubular reinforcing layer.

The metallic tubular reinforcing layer can be cut from a single continuous hypotube.

The deformations can be positioned to introduce a flexibility gradient in the metallic tubular reinforcing layer with increasing flexibility of the metallic tubular reinforcing layer in a distal direction as defined by orientation of the catheter during treatment.

Another example catheter can include an inner liner, a braided wire support structure disposed around the inner liner, a metallic tubular reinforcing layer disposed around the inner liner, an outer polymer layer disposed around the metallic tubular reinforcing layer and shaping an outer surface of the catheter, and protrusions extending from the outer surface of the catheter.

The protrusions can each have a hemispherical shape. The protrusions can be regularly spaced over at least a portion of the outer surface of the catheter. The catheter can have smooth regions lacking hemispherical protrusions and interrupting a spacing pattern of the hemispherical protrusions. The smooth regions can be on an exterior surface of the catheter. When applied to vascular tissue, the smooth regions can result in a higher coefficient of static friction compared to the exterior surface of the catheter having the spacing pattern of the hemispherical protrusions that is uninterrupted by the smooth regions.

The catheter can include fluid-filled cavities each respectively under one of the protrusions and shaped by the outer polymer layer. The fluid-filled cavities can each be configured to rupture to release fluid from the cavity in response to stresses induced on the respective protrusion during an intravascular treatment. The fluid can include an oil and/or a drug. The fluid can include a drug to inhibit vascular spasms, and the fluid-filled cavities can be configured to rupture in response to vascular spasms.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

DETAILED DESCRIPTION

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

When used herein, the terms "tubular" and "tube" are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered or curved outer surface without departing from the scope of the present invention.

The figures illustrate various example catheters 100, 200, 300 and catheter portions 100a-d, 300a-d having features that are combinable with each other to result in numerous catheter designs. A resulting catheter can vary in design along its length to achieve desired stiffness and/or trackability variations as understood by a person skilled in the pertinent art according to the teachings herein.

Figure 1:
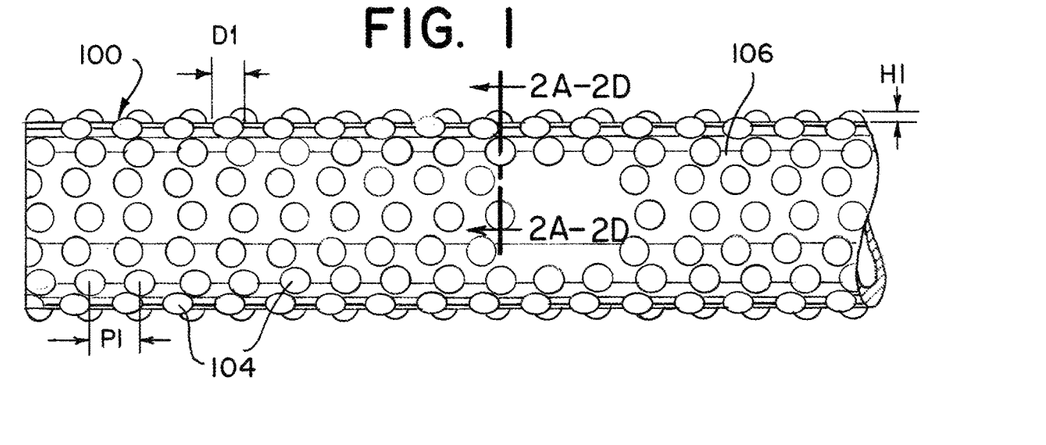
FIG. 1 is an illustration of an exterior surface of a portion of an example catheter having protrusions according to aspects of the present invention.

FIG. 1 is an illustration of an exterior surface of a portion of an example catheter 100 having protrusions (pimples) 104 extending from an otherwise smooth surface 106. The protrusions 104 are arranged and shaped to reduce friction between the exterior surface of the catheter 100 and vascular anatomy or an inner lumen of another catheter in contact with the exterior surface. Friction is reduced by reducing area of contact to the exterior surface to peaks of the protrusions 104; the smooth surface 106 is inhibited from contacting vascular anatomy or lumen of another catheter due to height of the protrusions 104. Reduced friction can result in reduced track forces and/or better ease of trackability.

Dimensions of the protrusions 104 can be described in relation to pimple diameter (D1), diameter of a circular base of a hemispherical protrusion, and pimple depth (H1), height of the protrusion 104 measured radially from the smooth surface 106. Spacing of the protrusions 104 in a regular pattern can be described in relation to pimple pitch (P1), distance between a center point of a base of the protrusion 104. Pimple diameter (D1), pimple pitch (P1), and pimple depth (H1) can be altered to achieve desired trackability of the exterior surface of the catheter 100. Additionally, or alternatively pimple diameter (D1), pimple pitch (P1), and pimple depth (H1) can be altered to achieve desired flexibility and/or flexibility gradient of the catheter 100, where typically the catheter is preferably stiffer near it's proximal end and becomes gradually more flexible toward its distal end.

FIGS. 2A through 2D are cross-sectional illustrations as indicated in FIG. 1 of example catheter constructions. Each cross-sectional illustration represents a respective catheter portion 100a-100d. Features of each cross-section 100a-100d can be combined to form various cross-sectional configurations as understood by a person skilled in the pertinent art according to the teachings herein.

Figures 2A, 2B:
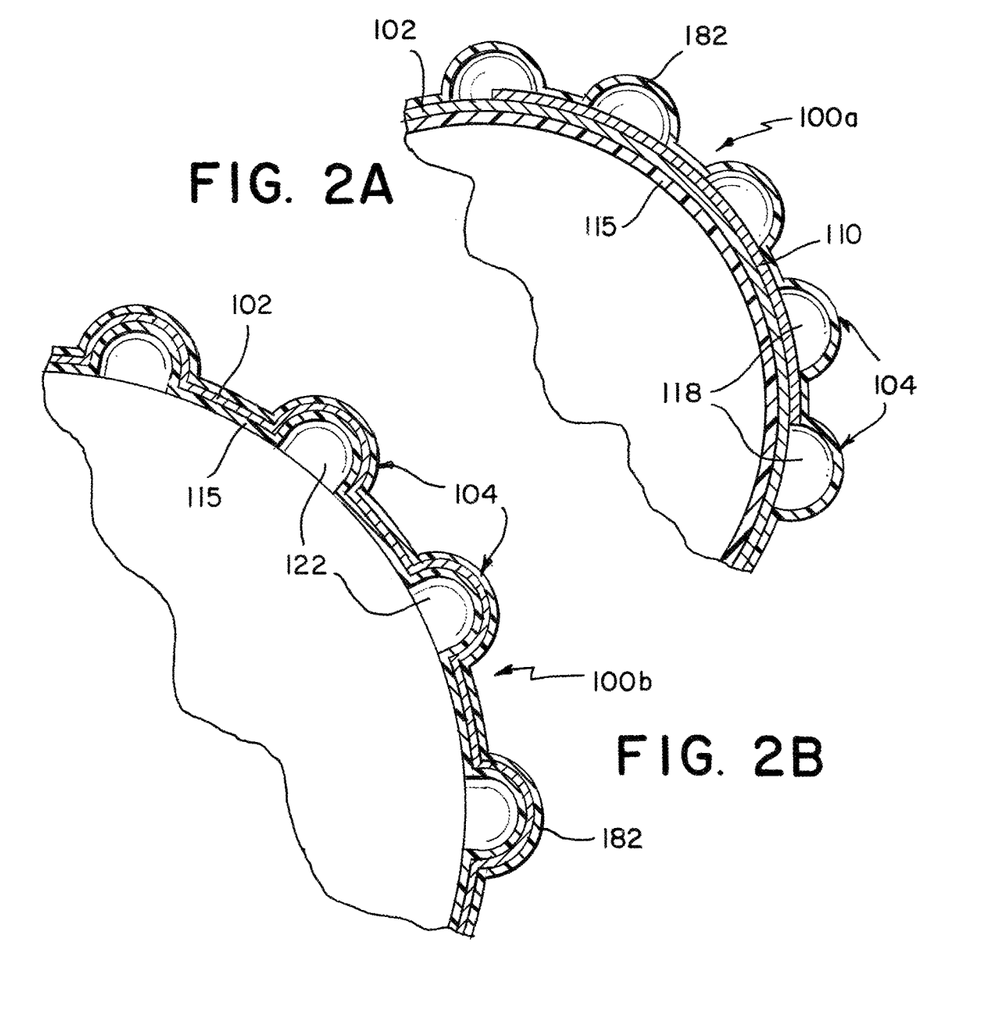
FIGS. 2A through 2D are cross-sectional illustrations as indicated in FIG. 1 of example catheter constructions according to aspects of the present invention.

FIG. 2A illustrates a catheter portion 100a having an inner liner 115 forming a smooth inner surface and an outer layer 182 shaped to form protrusions 104. The catheter portion 100a is illustrated including a middle braid layer 102 and a portion of a metallic tubular reinforcing layer 110 providing stability to the catheter. The metallic tubular reinforcing layer 110 can be configured similarly to the metallic tubular reinforcing layer 210 of an example catheter 200 illustrated in FIG. 3 and/or otherwise configured such as described in U.S. patent application Ser. No. 17/1147,725, filed Dec. 8, 2020, published as U.S. Patent Application Publication No. 2022/0176071 A1 dated Jun. 9, 2022. For instance, the cross-section of the metallic tubular reinforcing layer 110 illustrated in FIG. 2A can coincide with a ribbon cut segment 240 of the catheter 200 illustrated in FIG. 3.

The outer layer 182 can be constructed to retain the shape of the protrusions 104 during manipulation of the catheter. Alternatively, the outer layer 182 can be constructed so that it breaks or opens to release fluid in pimple cavities 118 under the protrusions 104 when the protrusions are pressed against by vasculature tissue and/or an interior lumen of another catheter, for example in a constricting or spasming vessel. Configured as such, the protrusions can burst as needed to facilitate tracking of the catheter portion 100a. In some examples, pimple cavities 118 can include a drug such as nitrous oxide to inhibit blood vessel spasms. Additionally, or alternatively, pimple cavities 118 can include a lubricant such as oil or heparin to cause the surface of the catheter portion 100a to be lubricious. Pimple cavities 118 having a lubricant or vasal dilator can facilitate insertion of the catheter portion 100a into a blood vessel having a smaller inner diameter than the outer diameter of the catheter portion 100a. Pressure of the blood vessel against the exterior surface of the catheter portion 100a can cause the outer layer 182 to burst, releasing lubricant and/or vasal dilator from pimple cavities 118 to cause the catheter portion 100a to slide more easily and/or increase inner diameter of the blood vessel.

FIG. 2B illustrates a catheter portion 100b having deformations each having a protrusion 104 on an exterior surface of the catheter portion 100b and an opposite indentation 122 on an interior surface of the catheter portion 100b. The catheter portion 100b includes an inner liner 115, a middle braid layer 102 and an outer layer 182 shaped collectively to form the deformations. The indentations 122 on the interior surface of the catheter portion 100b can result in lower track forces for devices being navigated through the lumen of the catheter portion 100b by reducing contact area between the interior surface of the catheter portion 100b and such devices. The indentations 122 on the interior surface of the catheter portion 100b can further result in the ability to aspirate or flush higher volumes of fluid through the lumen of the catheter portion 100b more efficiently by increase the overall internal volume of the catheter compared to a catheter having a similar inner diameter. This may be particularly beneficial when devices are placed in the lumen of the catheter portion 100b.

Figures 2C, 2D:
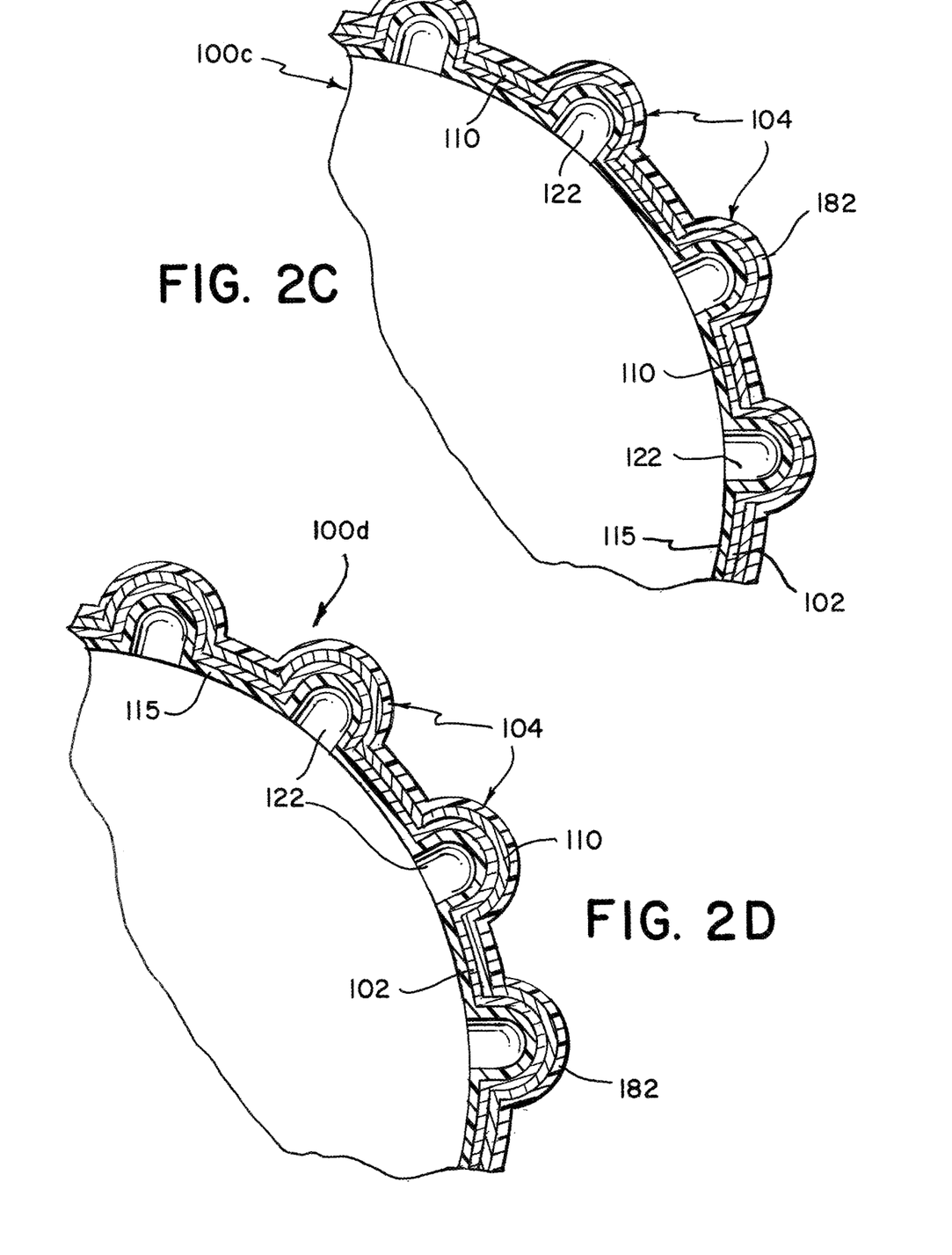

FIG. 2C illustrates a catheter portion 100c having deformations each having a protrusion 104 on an exterior surface of the catheter portion 100c and an opposite indentation 122 on an interior surface of the catheter portion 100c. The catheter portion 100c includes an inner liner 115, a middle braid layer 102, and an outer layer 182 shaped collectively to form the deformations similar to the catheter portion 100b illustrated in FIG. 2B. The catheter portion 100c additionally includes a metallic tubular reinforcing layer 110 having openings through which the deformations extend. The openings can be circular. The deformations can have a circular base with a circumference or diameter about equal to a circumference or diameter of the openings through which they respectively extend. For instance, the openings can be configured similarly to holes 220 in the metallic tubular reinforcing layer 210 of the catheter 200 illustrated in FIG. 3. Protrusions 104 can have a pimple diameter (D) about equal to a diameter of the hole through which each protrusion respectively extends.

FIG. 2D illustrates a catheter portion 100d having deformations each having a protrusion 104 on an exterior surface of the catheter portion 100d and an opposite indentation 122 on an interior surface of the catheter portion 100d. The catheter portion 100d includes an inner liner 115, a middle braid layer 102, a metallic tubular reinforcing layer 110, and an outer layer 182 shaped collectively to form the deformations.

Figure 3:
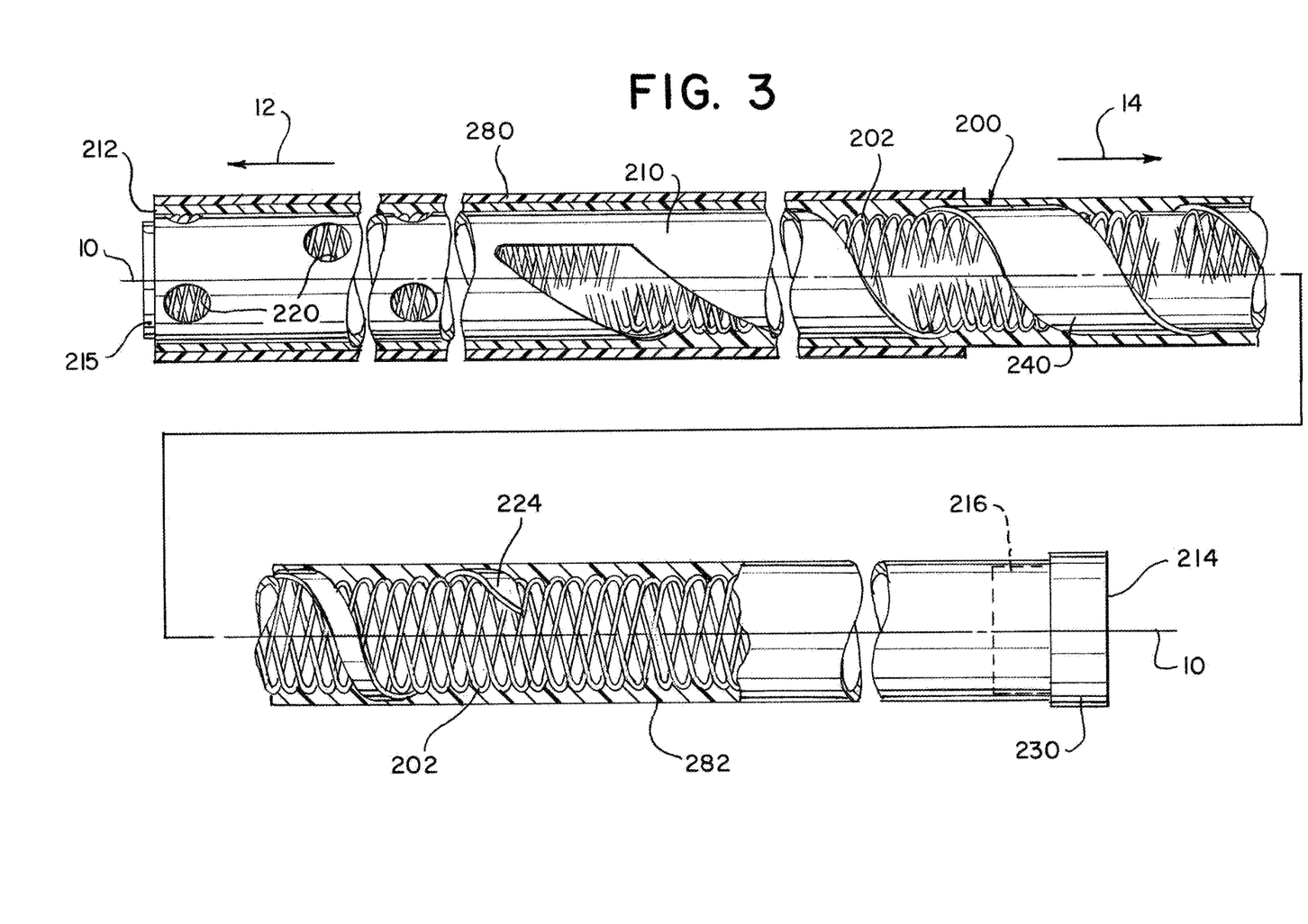
FIG. 3 is an illustration of an example catheter including a metallic tubular reinforcing layer according to aspects of the present invention.

FIG. 3 is an illustration of an example catheter 200 including a metallic tubular reinforcing layer 210. The construction of the catheter 200 and various configurations of the metallic tubular reinforcing layer 210 are described in greater detail in U.S. patent application Ser. No. 17/1147,725, filed Dec. 8, 2020, published as U.S. Patent Application Publication No. 2022/0176071 A1 dated Jun. 9, 2022. The metallic tubular reinforcing layer 210 is optional, as current typical catheter designs achieve stiffness by adding polymer layers in regions where increased stiffness is desired (typically increasing approaching a proximal end 212 of the catheter 200). The metallic tubular reinforcing layer 210 can be a replacement for the proximal portion of many current catheter shaft designs, which are plastic. The illustrated catheter 200 can be modified to include additional layers as understood by a person skilled in the pertinent art.

An innermost layer of the catheter 200 can include an inner liner 215 of PTFE or other low friction material to facilitate the passage of ancillary devices through the catheter lumen. Disposed around the inner liner 215 can be a braided wire support structure 220 with braids or windings involving wires or bands of other materials. The metallic tubular reinforcing layer 210 can be disposed over the braid 220. A polymer jacket 282 can be disposed over the braid 220 and metallic tubular reinforcing layer 210. An atraumatic polymer tip 230 can be disposed at a distal end 214 of the catheter 200. A radiopaque marker or band 216 (such as platinum) can be disposed adjacent to the tip 230 to mark the terminal end of the catheter 200 during a procedure.

The metallic tubular reinforcing layer 210 can extend from the proximal end 212 of the catheter 200 and terminate at a distal end 224 at some point proximal of the distal end 214 of the catheter 200, running at least a portion of the length of the catheter 200. The metallic tubular reinforcing layer 210 can be cut from a single continuous Nitinol hypotube or other suitable material.

Stiffness transitions along the axial length of the catheter 200 can be affected by cut patterns in the metallic tubular reinforcing layer 210 and/or positioning of protrusions 104 and/or indentations 122 along the catheter 200. The catheter 200 can include protrusions 104, indentations 122, and combinations thereof to achieve cross-sections similar to those illustrated in FIGS. 2A through 2D. Hemispherical or other atraumatic shaped deformations can be positioned to introduce a flexibility gradient in the metallic tubular reinforcing layer with increasing flexibility of the metallic tubular reinforcing layer 210 in a distal direction as defined by orientation of the catheter 200 during treatment. Pimple diameter (D), pimple pitch (P), and pimple depth (H) can be altered to achieve desired stiffness and stiffness gradient of the catheter 200. The cut pattern of the metallic tubular reinforcing layer 210 can define sidewall openings (e.g. holes 220, space between ribbon segment 240) through which some or all of the remaining layers 280, 202, 215 of the catheter 200 can extend to form protrusions 104 and/or indentations 122. Additionally, or alternatively, the metallic tubular reinforcing layer 210 can be shaped to form protrusions 104 and/or indentations 122.

Figure 4A:
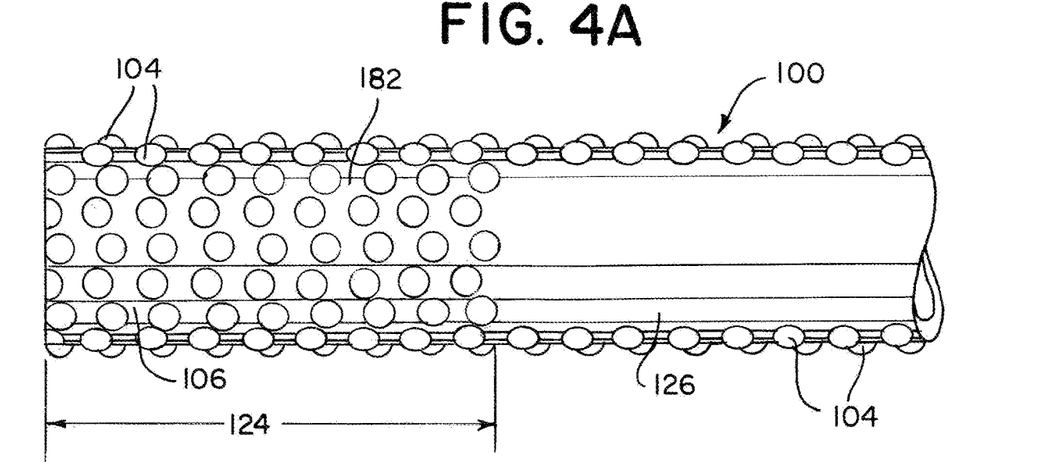
FIGS. 4A and 4B are illustrations of smooth regions of an example catheter according to aspects of the present invention.
Figure 4B:
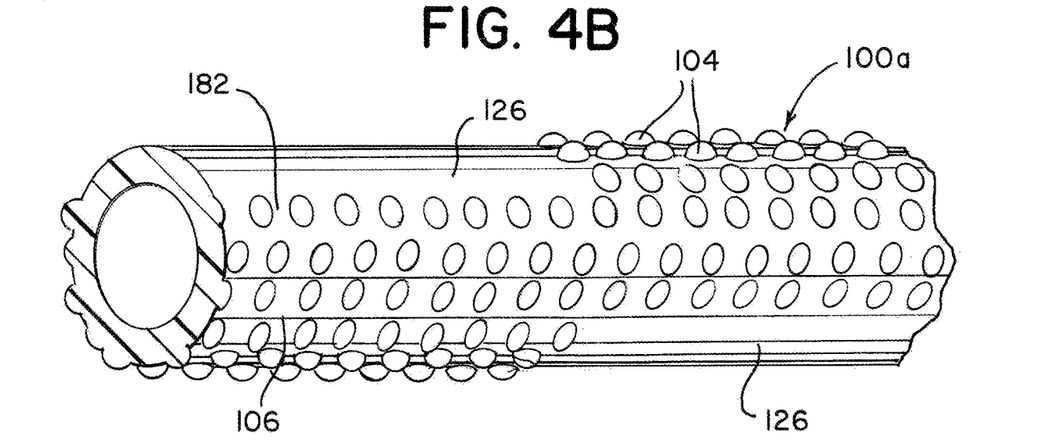

FIGS. 4A and 4B are illustrations of smooth regions 126 on the exterior surface of the example catheter 100. The exterior surface includes a first region 124 having protrusions 104 spaced in a pattern and a second region lacking protrusions 104, being substantially smooth, and having an area sufficiently large to interrupt the pattern of the portion of the deformations in the first region 124. When applied to vascular tissue, the smooth second region 126 can result in a higher coefficient of friction compared to the first region 124 having protrusions 104. The protrusions 104 can be spaced in the first region 124 in a regular pattern as illustrated and/or an irregular pattern.

The smooth regions 126 can provide higher friction anchor patches to allow the catheter 100 to anchor in place. When the catheter 100 is positioned within vasculature and devices or smaller catheters are pushed through the lumen of the catheter 100, friction between the anchor patches 126 and vascular walls can prevent the catheter 100 from shifting or backing out.

Additionally, or alternatively, the smooth regions 126 can define controlled bend locations of the catheter 100.

FIG. 4B is an isometric view of a catheter portion 100a having a smooth inner lumen surface.

Figure 5:
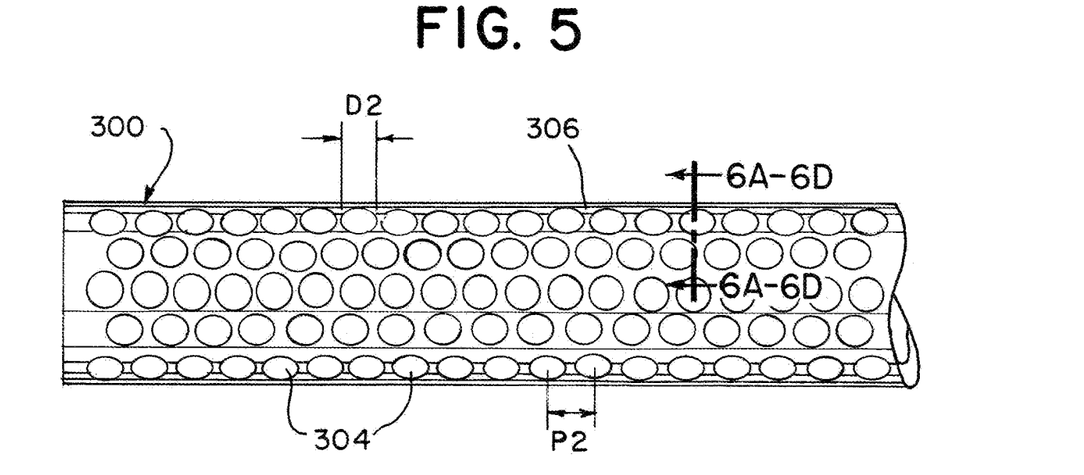
FIG. 5 is an illustration of an exterior surface of a portion of an example catheter having indentations according to aspects of the present invention.

FIG. 5 is an illustration of an exterior surface of a portion of an example catheter 300 having indentations (dimples) 304 extending into an otherwise smooth surface 306. The indentations 304 are arranged and shaped to reduce friction between the exterior surface of the catheter 300 and vascular anatomy or an inner lumen of another catheter in contact with the exterior surface. Friction is reduced by reducing area of contact to the smooth surface 306, A portion of the indentations 304 are inhibited from contacting vascular anatomy or lumen of another catheter due to depth of the indentations 304. Reduced friction can result in reduced track forces and/or better ease of trackability.

Dimensions of the indentations 304 can be described in relation to dimple diameter (D2), diameter of a circular base of a hemispherical indentation, and dimple depth (H2), depth of the indentation 304 measured radially inward from the smooth surface 306. Spacing of the indentations 304 in a regular pattern can be described in relation to dimple pitch (P2), distance between a center point of a base of the indentation 304. Dimple diameter (D2), dimple pitch (P2), and dimple depth (H2) can be altered to achieve desired trackability of the exterior surface of the catheter 300. Additionally, or alternatively dimple diameter (D2), dimple pitch (P2), and dimple depth (H2) can be altered to achieve desired flexibility and/or flexibility gradient of the catheter 300, where typically the catheter is preferably stiffer near it's proximal end and becomes gradually more flexible toward its distal end.

FIGS. 6A through 6D are cross-sectional illustrations as indicated in FIG. 5 of example catheter constructions. Each cross-sectional illustration represents a respective catheter portion 300a-300d. Features of each cross-section 300a-300d can be combined to form various cross-sectional configurations. Further, features of each cross-section 100a-100d illustrated in FIGS. 2A through 2D can be combined with features of each cross-section in FIGS. 6A through 6D to result in various cross-sections as understood by a person skilled in the pertinent art according to the teachings herein.

Figures 6A, 6B, 6C:
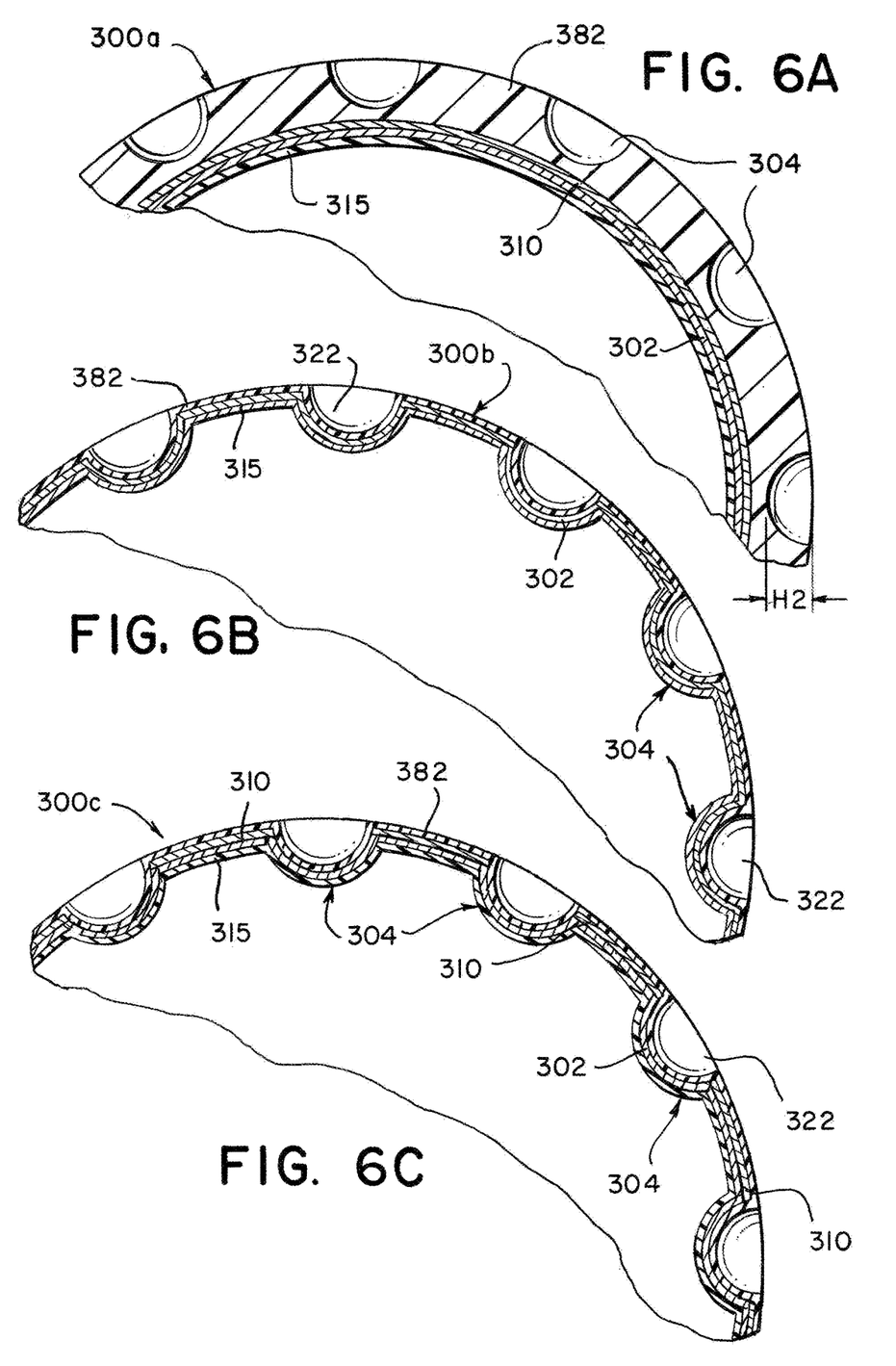
FIGS. 6A through 6D are cross-sectional illustrations as indicated in FIG. 5 of example catheter constructions according to aspects of the present invention.

FIG. 6A illustrates a catheter portion 300a having an inner liner 315 forming a smooth inner surface and an outer layer 382 shaped to form indentations 304. The catheter portion 300a is illustrated including a middle braid layer 302 and a portion of a metallic tubular reinforcing layer 310 providing stability to the catheter. The metallic tubular reinforcing layer 310 can be configured similarly to the metallic tubular reinforcing layer 210 of an example catheter 200 illustrated in FIG. 3 and/or otherwise configured such as described in U.S. patent application Ser. No. 17/1147,725, filed Dec. 8, 2020, published as U.S. Patent Application Publication No. 2022/0176071 A1 dated Jun. 9, 2022. For instance, the cross-section of the metallic tubular reinforcing layer 310 illustrated in FIG. 6A can coincide with a ribbon cut segment 240 of the catheter 200 illustrated in FIG. 3. As illustrated, the indentations 304 are formed exclusively by the outer layer 382 while the reinforcing layer 310 and braid layer 302 are smooth. The outer layer 382 therefore has a greater thickness than the other layers 310, 302, 315 and the indentations 304 are inset into the outer layer 382.

FIG. 6B illustrates a catheter portion 300b having deformations each having an indentation 304 on an exterior surface of the catheter portion 300b and an opposite protrusion 322 on an interior surface of the catheter portion 300b. The catheter portion 300b includes an inner liner 315, a middle braid layer 302 and an outer layer 382 shaped collectively to form the deformations. The protrusions 322 on the interior surface of the catheter portion 300b can result in lower track forces for devices being navigated through the lumen of the catheter portion 300b by reducing contact area between the interior surface of the catheter portion 300b and such devices and therefore friction.

FIG. 6C illustrates a catheter portion 300c having deformations each having an indentation 304 on an exterior surface of the catheter portion 300c and an opposite protrusion 322 on an interior surface of the catheter portion 300c. The catheter portion 300c includes an inner liner 315, a middle braid layer 302, and an outer layer 382 shaped collectively to form the deformations similar to the catheter portion 300b illustrated in FIG. 6B. The catheter portion 300c additionally includes a metallic tubular reinforcing layer 310 having openings through which the deformations extend. The openings can be circular. The deformations can have a circular base with a circumference or diameter about equal to a circumference or diameter of the openings through which they respectively extend. For instance, the openings can be configured similarly to holes 220 in the metallic tubular reinforcing layer 210 of the catheter 200 illustrated in FIG. 3.

Figures 6D, 7A:
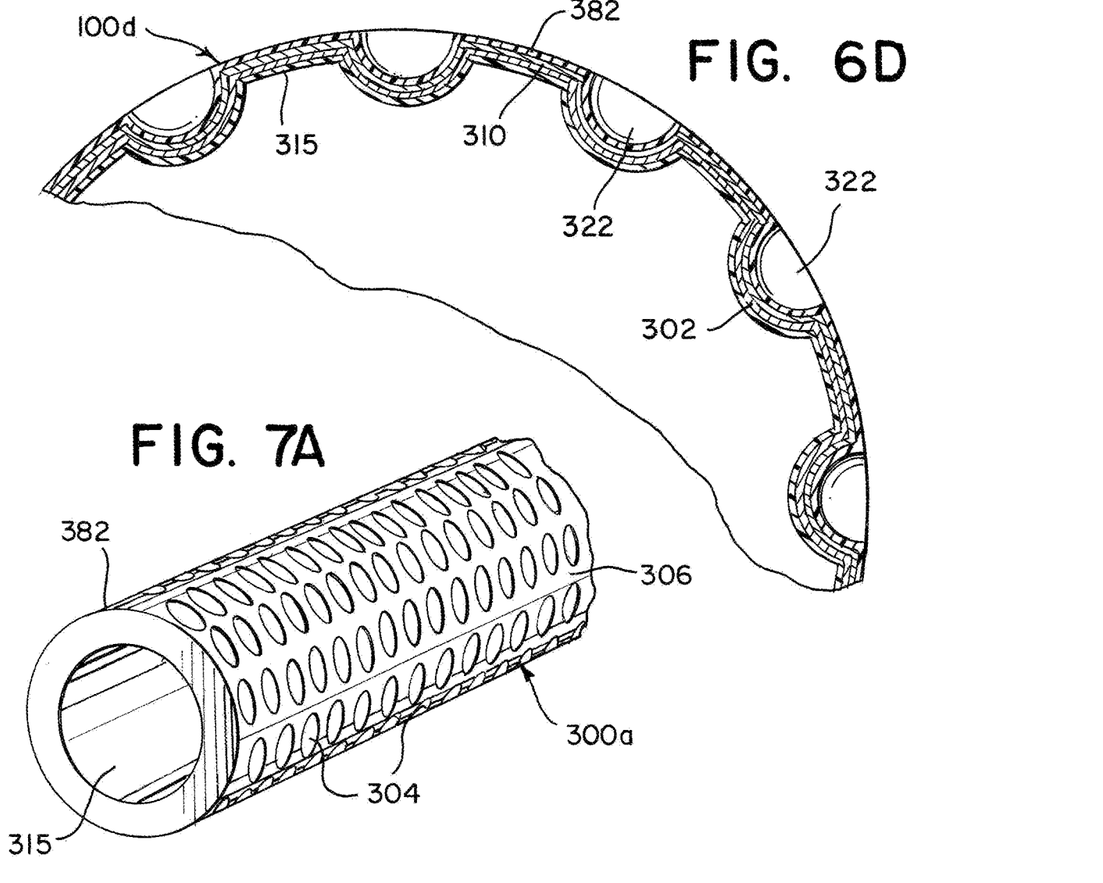
FIG. 7A is an isometric view of a portion of an example catheter including indentations on the exterior surface according to aspects of the present invention.

FIG. 6D illustrates a catheter portion 600d having deformations each having an indentation 304 on an exterior surface of the catheter portion 300d and an opposite protrusion 322 on an interior surface of the catheter portion 300d. The catheter portion 300d includes an inner liner 315, a middle braid layer 302, a metallic tubular reinforcing layer 310, and an outer layer 382 shaped collectively to form the deformations.

FIG. 7A is an isometric view of a portion of an example catheter portion 300a including indentations 304 on the exterior surface and a smooth interior lumen surface 315.

Figure 7B:
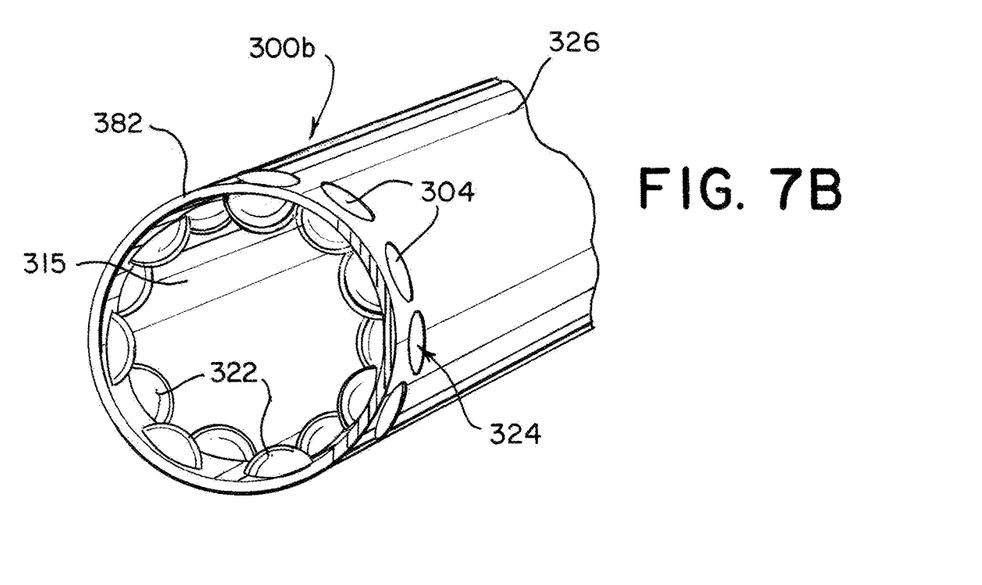
FIG. 7B is an isometric view of a portion of an example catheter including indentations on the exterior surface and corresponding protrusions on an interior surface according to aspects of the present invention.

FIG. 7B is an isometric view of a portion of an example catheter portion 300b including indentations 3-4 on the exterior surface and corresponding protrusions 322 on an interior surface 315. The catheter portion 300b further includes an anchor patch region 326 configured similarly to anchor patch regions 126 illustrated in FIGS. 4A and 4B.

The descriptions contained herein are examples of embodiments of the invention and are not intended to limit the scope of the invention. As described herein, the invention contemplates many variations and modifications of the catheter, including alternative materials, alternative geometries, alternative structures, combinations with compatible structures, etc. For instance, protrusions and indentations drawn herein as hemispherical can have an arbitrary atraumatic shape including dome, ridge, or trough. Methods of treatment using an example catheter and methods of construction of an example catheter are within the scope of the present disclosure. Modifications apparent to those skilled in the pertinent art are intended to be within the scope of the claims which follow.

The invention claimed is:

1. A catheter comprising:
   a first tubular surface;
   a second tubular surface opposite the first tubular surface;
   a plurality of deformations each comprising an indentation on the first tubular surface and a corresponding protrusion on the second tubular surface opposite the indentation;
   a metallic tubular reinforcing layer comprising a sidewall opening through which an inner liner and a braided wire support structure, disposed around the inner liner, protrude to shape at least one deformation of the plurality of deformations; and
   an outer polymer layer disposed around the metallic tubular reinforcing layer,
   wherein the plurality of deformations are shaped by the outer polymer layer,
   wherein the plurality of deformations are positioned to introduce a flexibility gradient in the metallic tubular reinforcing layer with increasing flexibility of the metallic tubular reinforcing layer in a distal direction as defined by orientation of the catheter during treatment, and
   wherein the metallic tubular reinforcing layer comprises ribbon cut segments.

2. The catheter of claim 1,
   wherein the indentation and the corresponding protrusion of each of the plurality of deformations are respectively hemispherical in shape.

3. The catheter of claim 1, wherein the first tubular surface is an interior surface of the catheter and the second tubular surface is an exterior surface of the catheter.

4. The catheter of claim 1, wherein the first tubular surface is an exterior surface of the catheter and the second tubular surface is an interior surface of the catheter.

5. The catheter of claim 1, further comprising:
   a first region of the catheter comprising at least a portion of the plurality of deformations spaced in a regular pattern; and
   a second region lacking the plurality of deformations, being substantially smooth at least on an exterior surface of the catheter, and comprising an area sufficiently large to interrupt the regular pattern of the portion of the plurality of deformations in the first region,
   wherein, when the exterior surface of the catheter including the first and second regions is applied to vascular tissue, contact between the second region and vascular tissue results in a higher coefficient of static friction compared to a coefficient of static friction between the first region and vascular tissue.

6. The catheter of claim 1,
   wherein the metallic reinforcing layer is disposed around the braided wire support structure, and
   wherein the plurality of deformations are shaped by the inner liner, the braided wire support structure, and the outer polymer layer.

7. The catheter of claim 1, wherein the metallic tubular reinforcing layer is shaped to form at least one of the plurality of deformations.

8. The catheter of claim 1,
   wherein the sidewall opening comprises a circular shape comprising a circumference, and
   wherein the at least one of the plurality of deformations protruding through the sidewall opening is a single deformation and comprises a hemispherical shape comprising a circumference about equal to that of the circumference of the circular shape of the sidewall opening.

9. The catheter of claim 1, wherein the sidewall opening comprises a helical shape circumscribing the catheter.

10. The catheter of claim 1, wherein at least one of the plurality of deformations is further shaped by the metallic tubular reinforcing layer.

11. The catheter of claim 1, wherein the metallic tubular reinforcing layer is cut from a single continuous hypotube.

12. The catheter of claim 1, wherein one or more of a spacing, diameter, pitch, depth, diameter of a circular base of a deformation of the plurality of deformations, and height of the plurality of deformations are selected to introduce a flexibility gradient in the metallic tubular reinforcing layer with increasing flexibility of the metallic tubular reinforcing layer in a distal direction as defined by orientation of the catheter during treatment.

13. A catheter comprising:
   an inner liner;
   a braided wire support structure disposed around the inner liner;
   a metallic tubular reinforcing layer disposed around the braided wire support structure;
   an outer polymer layer disposed around the metallic tubular reinforcing layer and shaping an outer surface of the catheter; and
   protrusions extending from the outer surface of the catheter,
   wherein the protrusions are shaped by the inner liner, the braided wire support structure, and the outer polymer layer,
   wherein the metallic tubular reinforcing layer comprises a sidewall opening through which the inner liner and the braided wire support structure protrude to shape at least one of the protrusions,
   wherein the protrusions are positioned to introduce a flexibility gradient in the metallic tubular reinforcing layer with increasing flexibility of the metallic tubular reinforcing layer in a distal direction as defined by orientation of the catheter during treatment, and
   wherein the metallic tubular reinforcing layer comprises ribbon cut segments.

14. The catheter of claim 13,
   wherein the protrusions each comprise a hemispherical shape, and
   wherein the protrusions are regularly spaced over at least a portion of the outer surface of the catheter.

15. The catheter of claim 14, further comprising:
   a plurality of smooth regions lacking the hemispherical protrusions and interrupting a spacing pattern of the hemispherical protrusions.

16. The catheter of claim 15,
   wherein the smooth regions are on the outer surface of the catheter, and
   wherein when applied to vascular tissue, the smooth regions result in a higher coefficient of static friction compared to the outer surface of the catheter having the spacing pattern of the hemispherical protrusions that is uninterrupted by the smooth regions.

17. The catheter of claim 13, wherein the metallic tubular reinforcing layer is shaped to form at least one of the protrusions.

18. The catheter of claim 13, wherein one or more of a spacing, diameter, pitch, diameter of a circular base of at least one of the protrusions, and height of the protrusions are selected to introduce a flexibility gradient in the metallic tubular reinforcing layer with increasing flexibility of the metallic tubular reinforcing layer in a distal direction as defined by orientation of the catheter during treatment.

19. The catheter of claim 13, further comprising:
a plurality of fluid-filled cavities each respectively under one of the protrusions and shaped by the outer polymer layer, the fluid-filled cavities each being configured to rupture to release fluid from the cavity in response to stresses induced on the respective protrusion during an intravascular treatment.

* * * * *